United States Patent [19]
Dunn et al.

[11] Patent Number: 5,464,934
[45] Date of Patent: Nov. 7, 1995

[54] METAL CHELATES AS SPACER COMPOUNDS IN BIOLOGICALLY ACTIVE PEPTIDES

[75] Inventors: T. Jeffrey Dunn, Cedar Hill; Ananthachari Srinivasan, St. Chalres; Leon R. Lyle, Webster Groves; Raghavan Rajagopalan, Maryland Heights, all of Mo.

[73] Assignee: Mallinckrodt Medical, Inc., St. Louis, Mo.

[21] Appl. No.: 63,172

[22] Filed: May 14, 1993

[51] Int. Cl.$^6$ .................... C07K 5/00; C07K 7/00; C07K 17/00; A61K 49/00
[52] U.S. Cl. .................... 530/326; 530/327; 530/328; 530/329; 530/330
[58] Field of Search .................... 530/326, 327, 530/328, 329, 330; 424/1.1, 1.41, 1.45, 1.53, 1.49, 1.69

[56] References Cited

U.S. PATENT DOCUMENTS

| | | | |
|---|---|---|---|
| 4,727,028 | 2/1988 | Santerri et al. | 435/240.2 |
| 4,738,921 | 4/1988 | Belagaje et al. | 435/68 |
| 4,816,561 | 3/1989 | Torado | 530/324 |
| 4,849,511 | 7/1989 | Verbruggen | 534/14 |
| 4,885,277 | 12/1989 | Nawroth et al. | 514/15 |
| 4,925,650 | 5/1990 | Nosco et al. | 424/1.11 |
| 4,980,147 | 12/1990 | Fritzberg et al. | 424/1.11 |
| 4,992,373 | 2/1991 | Bang et al. | 435/226 |
| 5,015,729 | 5/1991 | Speiss et al. | 530/350 |

FOREIGN PATENT DOCUMENTS 0215496  of 1991  Japan.

OTHER PUBLICATIONS

Merrifield, J. Am. Chem. Soc., vol. 85, 2149 (1963).

Maraganore et al Biochemistry 29, 7095–7107 (1990).

*Primary Examiner*—Jill Warden
*Assistant Examiner*—Sheela J. Huff
*Attorney, Agent, or Firm*—Thomas P. McBride; Brian K. Stierwalt

[57] ABSTRACT

Ligands that are capable of forming metal complexes are incorporated directly into peptides at nonbiologically active locations. The metal complex serves as a bifunctional agent and as a spacer molecule. In one aspect of the invention, the ligands are prepared by replacing a nonbiologically active peptide spacer sequence with either Cys-Gly-Gly-Glu(γ-)CO- (SEQ ID NO:1) or Cys-Gly-Gly-Lys(ε-)NH-CO(CH$_2$)$_2$-CO- (SEQ ID NO:2). In these examples, unnatural peptide bonds are used to attach the ligand to the terminal end of the peptide. Peptides incorporating such ligands are also disclosed.

Other spacer ligands which may be incorporated into peptides include the following natural peptide sequences: -Cys-Gly-His-, -Asp-Gly-Cys-, -Glu-Gly-Cys-, -Gly-Asp-Cys-, and -Gly-Glu-Cys-. Unnatural tripeptides which function as spacer ligands include: -Cys-Gly-(imidazolyl glycyl)-, -iso-Cys-Gly-(imidazolyl glycyl)-, and -isoCys-Gly-His-. When the above peptide sequences are present in a nonbiologically active peptide spacer, they are able to form metal complexes with desired metal ions, and the resulting complexes serve as bifunctional agents and as spacer molecules in the peptide.

10 Claims, No Drawings

METAL CHELATES AS SPACER COMPOUNDS IN BIOLOGICALLY ACTIVE PEPTIDES

BACKGROUND

1. Field of the Invention

This invention relates generally to bifunctional chelating agents for use with biologically active peptides. More particularly, the present invention relates to the incorporation of ligands directly into peptides at nonbiologically active locations such that the ligand will bind the desired metal ion and the resulting complex will serve as a bifunctional agent and as a spacer molecule.

2. Technology Background

Scintigraphic imaging and similar radiographic techniques for visualizing tissues in vivo are finding ever-increasing application in biological and medical research and in diagnostic and therapeutic procedures. Generally, scintigraphic procedures involve the preparation of radioactive agents which upon introduction to a biological subject, become localized in the specific organ, tissue or skeletal structure of choice. When so localized, traces, plots or scintiphotos depicting the in vivo distribution of radiographic material can be made by various radiation detectors, e.g., traversing scanners and scintillation cameras. The distribution and corresponding relative intensity of the detected radioactive material not only indicates the space occupied by the targeted tissue, but also indicates a presence of receptors, antigens, aberrations, pathological conditions, and the like.

In general, depending on the type of radionuclide and the target organ or tissue of interest, the compositions comprise a radionuclide, a carrier agent such as a biologically active protein or peptide designed to target the specific organ or tissue site, various auxiliary agents which affix the radionuclide to the carrier such as bifunctional chelating agents, water or other delivery vehicles suitable for injection into, or aspiration by, the patient, such as physiological buffers, salts, and the like. The auxiliary agent attaches or complexes the radionuclide to the peptide carrier agent, which permits the radionuclide to localize where the carrier agent concentrates in the biological subject.

Often the biologically active protein or peptide has one or more bioactive sites separated by nonbiologically active peptide sequences. For example, Hirulog, a thrombin binding peptide, contains a spacer constructed between a catalytic binding site tripeptide and a 12-mer sequence necessary for anion binding excosite (ABE) site binding. In the Biogen hirudin analog, D-Phe-Pro-Arg-(Gly)$_n$-Asn-Gly-Asp-Phe-Glu-Glu-Ile-Pro-Glu-Glu-Tyr-Leu, the polyglycine unit with n from 4 to 8 merely acts as a spacer. In thrombin binding assays, replacement of tetraglycine with hexa- and octaglycine units have very little effect on the binding constants, $K_i$. J. M. Maraganore, P. Bourdon, J. Jabloski, K. L. Ramachandran, J. W. Fenton, *Biochemistry*, vol. 29, pp. 7095 (1990).

There are other examples of biologically active peptides having nonbiologically active spacers. For example, in Melanin Concentrating Hormone (MCH), 7-amino-hepatanoic acid has been used as a liner replacement of cystine. D. W. Brown et al., *Biopolymers*, vol. 29, p. 609 (1990). In addition, analogs of Atrial Natriuretic Factor (ANF) have been prepared using -HN(CH$_2$CH$_2$CH$_2$)$_3$CH$_2$CO- and -HN(CH$_2$CH$_2$O)$_3$CH$_2$CO. These fragments replace tetraamino acid residues in the ANF. D. Boumrah, et al. *Tetrahedron Letters*, vol. 32, no. 52, p. 7735 (1991).

When using biologically active peptides which have non-biologically active spacers, it is important that the bifunctional chelating agent not destroy the peptides's bioactivity. If the peptide's bioactivity is destroyed, then the peptide subsequently labeled with a radioisotope will have little value in diagnostic or therapeutic application.

It will be appreciated that it would be an advancement in the art to provide ligands capable of forming chelate complexes with diagnostic and therapeutic radioisotopes which can be incorporated directly into peptides at nonbiologically active locations such that the ligands function as spacer compounds.

Such ligands and methods of incorporating the ligands into peptides are disclosed and claimed herein.

BRIEF SUMMARY OF THE INVENTION

The present invention relates to ligands and to methods of incorporating the ligands and metal complexes as spacer compounds into biologically active peptides. In one aspect of the present invention the ligands are prepared by replacing a nonbiologically active peptide chain with either Cys-Gly-Gly-Glu($\gamma$-)CO- (SEQ ID NO:1) or Cys-Gly-Gly-Lys($\epsilon$-)NH-CO(CH$_2$)$_2$-CO- (SEQ ID NO:2). Unnatural peptide bonds are used to attach the ligand to the terminal end of the peptide. For example, the $\gamma$-carboxylic acid of glutamic acid and the $\epsilon$-amine of lysine are used. Thus, the ligand-forming peptide sequence which replaces the non-biologically active peptide chain is attached to the biologically active peptide portion through an unnatural peptide bond.

In another aspect of the present invention, the ligand-forming spacer compound is formed from one of the following natural tripeptide sequences:

-Cys-Gly-His-
-Asp-Gly-Cys-
-Glu-Gly-Cys-
-Gly-Asp-Cys-
-Gly-Glu-Cys-

When one of the above tripeptide sequences is present in a nonbiologically active peptide spacer, it is able to form chelate complexes with radionuclides. Similarly, the following unnatural peptide sequences may be used as ligand-forming spacer compounds:

-Cys-Gly-(imidazolyl glycyl)- -isoCys-Gly-(imidazolyl glycyl)-
-isoCys-Gly-His

The present invention is also directed to peptides having one of the above ligand-forming spacer compounds incorporated therein and to metal complexes of such ligands.

DETAILED DISCLOSURE OF THE INVENTION

The present invention relates to the incorporation of ligands as spacer compounds into biologically active peptides. For example, in the case of the Biogen hirudin analog D-Phe-Pro-Arg-(Gly)$_{4-8}$-Asn-Gly-Asp-Phe-Glu-Glu-Ile-Pro-Glu-Glu-Tyr-Leu, mentioned above, the nonbiologically active (Gly)$_{4-8}$ spacer located between the catalytic site binding tripeptide and the ABE site binding sequence dodecapeptide is replaced with either Cys-Gly-Gly-Glu($\gamma$-)CO- (SEQ ID NO:1) (1) or Cys-Gly-Gly-Lys($\epsilon$-)NH-CO(CH$_2$)$_2$-CO- (SEQ ID NO:2) (2). These fragments (1) and (2) can be prepared as a block (with proper protecting groups) or the orthogonally protected PG-Glu($\alpha$-COOPG')($\gamma$-)COOH and PG-Lys($\alpha$-COOPG')($\epsilon$-)NH-CO(CH$_2$)$_2$-CO- can be synthesized for introduction in a peptide synthesizer using the solid phase Merrifield peptide synthesis procedure using (phenylacetamido)methyl ("PAM") resin.

In both cases, the distal functional group of Glu or Lys is used for chain elongation instead of a simple glycine so that a 6,5,5-$N_3S$ core is produced after metal incorporation. The α-acid function in the amino acid after the diglycine unit is maintained in either case. Such a restriction demands that the protecting group be stable during trifluoroacetic acid removal of N-t-Boc (N-tertbutyloxycarbonyl), during further introduction of amino acids, and during use of HF/anisole for final cleavage of the peptide from the resin, but the protecting group should be removable under conditions that preserve the biological activity of the peptide. The use of trichloroethyl ("Tce", $CH_2CCl_3$) ester at the α-position of Gly and Lys during peptide synthesis in a synthesizer meets these conditions.

The trichloroethyl ester protecting group is stable to trifluoroacetic acid and HBr-HOAc, and it is expected to be stable in anhydrous HF for cleavage from the resin, making it an ideal choice as a protecting group. After cleavage from the resin, the Tce protecting group is removed using Zn-HOAc (zinc and acetic acid).

removal of trichloroethyl (Tce) group. This protecting group is especially useful for forming disulfides, if necessary. S-trichloroethoxycarbonyl is an alternative protecting group for use in the present invention. Assuming S-tri-chloroethoxycarbonyl is stable for HF cleavage, all the protecting groups can be removed simultaneously. Introduction of t-Boc-Glu(α-COOTce)-γ-COOH (5) or t-Boc-Lys(α-COOTce)-ε-NH-CO($CH_2$)-COOH (6) individually, followed by t-Boc(S-PG)Cys-COOH (7) (protecting group is Tcam or COOTce) at the appropriate locations should give similar results.

Peptides having the above ligand-forming spacer compounds (SEQ ID NO:1 and SEQ ID NO:2) incorporated therein have the following general formulae:

$(AA_1\text{-}AA_2)_n\text{-Cys-Gly-Gly-Glu}(\gamma\text{-})CO\text{-}(AA_3\text{-}AA_4)_m (AA_1\text{-}AA_2)_n\text{-}$
$Cys\text{-}Gly\text{-}Gly\text{-}Lys(\epsilon\text{-})NH\text{-}CO(CH_2)_2\text{-}CO\text{-}(AA_3\text{-}AA_4)_m$ wherein $(AA_1\text{-}AA_2)_n$ is a peptide chain of length n; $(AA_3\text{-}AA_4)_m$ is a peptide chain of length m; n and m may range from 0 to 20; and the sum n+m is greater than about 5 and less than about 20. When complexed with a suitable radionuclide, the peptides have the following general structures:

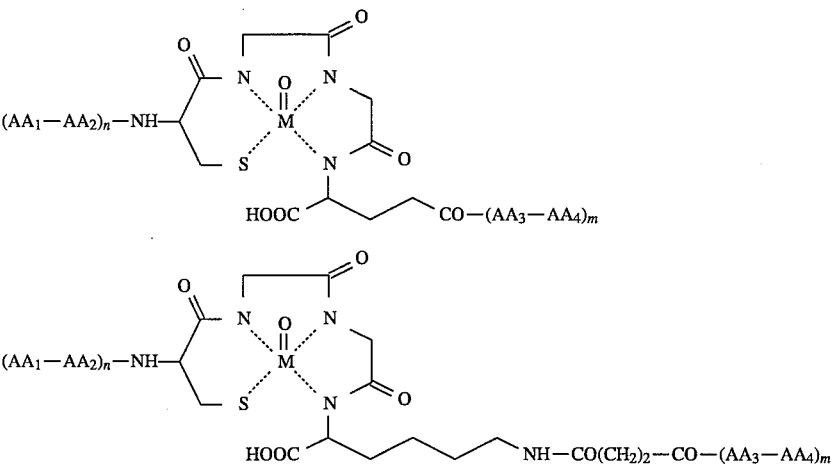

It is important to note that unnatural peptide bonds are used to attach the ligand to the terminal ends of the peptide. For example, the γ-carboxylic acid of glutamic acid and the ε-amine of lysine are used. Thus, the ligand-forming peptide sequence which replaces the nonbiologically active peptide chain is attached to the biologically active peptide portions through unnatural peptide bonds.

Fragments 1 (SEQ ID NO:1) or 2 (SEQ ID NO:2) can best be introduced into peptides by using the protected forms 3 or 4, respectively.

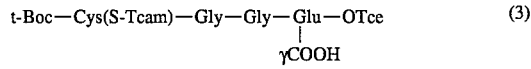

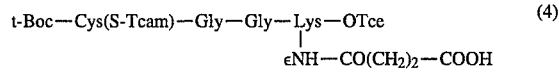

The preferred protecting group for cysteine in this method in trimethylacetamidomethyl (Tcam) group (*Tetrahedron Letters*, vol. 30, pp. 1979–1982 (1989)). Tcam protecting group is stable to HF cleavage and avoids many of the side reactions of conventional acetamidomethyl protecting group. Tcam can be removed by iodine-ethanol after the Where M is a diagnostic or therapeutic radioisotope known in the art such as γ-emitting radionuclides $^{67}$Ga, $^{111}$In, $^{99m}$Tc, $^{169}$Yb, $^{201}$Tl; β-emitting radionuclides $^{90}$Y, $^{67}$Cu, $^{186}$Re, $^{188}$Re, $^{169}$Er, $^{121}$Sn, $^{127}$Te, $^{143}$Pr, $^{198}$Au, $^{109}$Pd, $^{165}$Dy, $^{142}$Pr, $^{177}$Lu, $^{166}$Ho, $^{153}$Sm, $^{90}$Y, $^{89}$Sr, and $^{105}$Rh; or α-emitters $^{212}$Bi, $^{211}$At, $^{241}$Am, and $^{255}$Fm.

In both the above cases, the α-acid group in Glu and Lys is left free to provide a $N_3S$ core for complex formation. With the presence of cysteine and an α-carboxylic acid after the diglycine unit, a thermodynamically favored $N_3S$ core will exist over the other possible sites within the peptide. Thus, using the compositions and methods within the scope of the present invention it is possible discriminate between possible complex formation sites. In $N_3S$ systems of the present invention, the presence of -COOH closer to the core is the preferred site of complex formation.

The designs described above will allow one to rapidly synthesize bioactive peptides, such as Hirulog, Melanin Concentrating Hormone (MCH), and Atrial Natriuretic Factor (ANF) and analogs thereof, by using a peptide synthesizer. In both cases, 6,5,5-$N_3S$ ligands are the products. The ligands are positioned between the catalytic binding site and ABE binding site and should not affect the bioactivity of the peptide.

There is an important additional advantages of ligand design 3. Studies have shown that the kidney is highly active in the accumulation and degradation of γ-glutamyl derivatives of amino acids and peptides [*Eur. J. Biochemistry*, vol. 71, p. 549 (1976), *Biochem. J.*, vol. 170, p. 415 (1978)]. The enzyme, γ-glutamyl transferase occurring at high levels in the kidney is responsible for cleaving the γ-glutamyl-amide bond. This was the rationale behind the design of L-γ-gludopa and N-acyl-γ-glutamyl-sulfamethoxazole for organ specific delivery of glutamine and sulfamethoxazole. If small peptides containing radioactivity (especially therapeutic doses) tend to be retained in the kidney, the γ-glutamyl peptide bond can be introduced into the peptide as a cleavable linker to aid in elimination. In this case, the action of γ-glutamyl transferase is expected to produce smaller fragments that are eliminated via renal system.

Other ligand-forming spacer compounds which may be incorporated into peptides include the following natural peptide sequences:

-Cys-Gly-His-
-Asp-Gly-Cys-
-Glu-Gly-Cys-
-Gly-Asp-Cys-
-Gly-Glu-Cys-

When one of the above tripeptide sequences is present in a nonbiologically active peptide spacer, it is able to form chelate complexes with radionuclides. When complexed with a suitable radionuclide, such peptides have the following general structures:

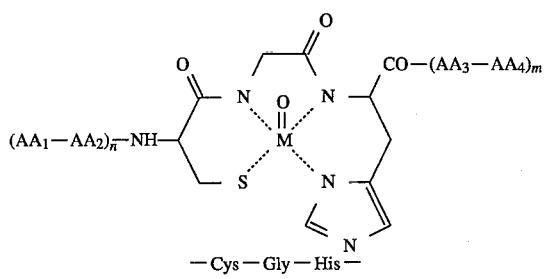

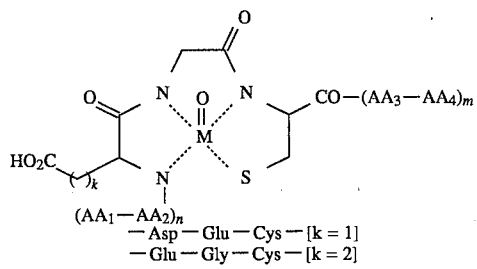

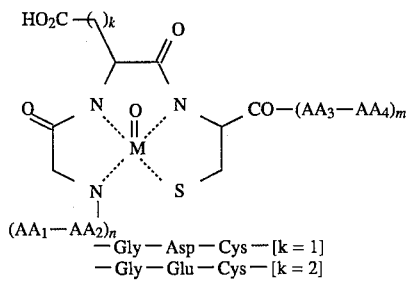

As used herein $(AA_1-AA_2)_n$ is a peptide chain of length n; $(AA_3-AA_4)_m$ is a peptide chain of length m; n and m may range from 0 to 20; and the sum n+m is greater than about 5 and less than about 20.

Similarly, the following unnatural peptide sequences may be used as ligand-forming spacer compounds:

-Cys-Gly-(imidazolyl glycyl)- -isoCys-Gly-(imidazolyl glycyl)-
-isoCys-Gly-His-

When the above peptide sequences are present in a nonbiologically active peptide spacer, they are able to form chelate complexes with radionuclides. Such peptides, when complexed with a suitable radionuclide, have the following general structures:

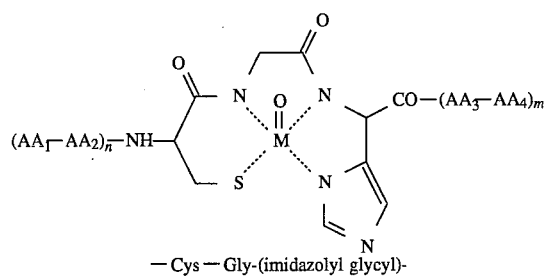

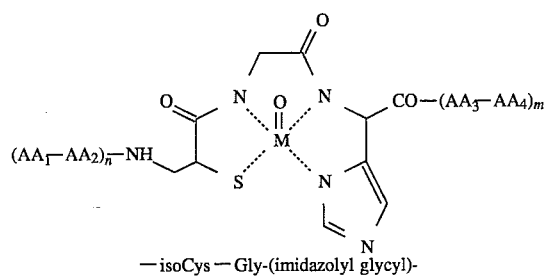

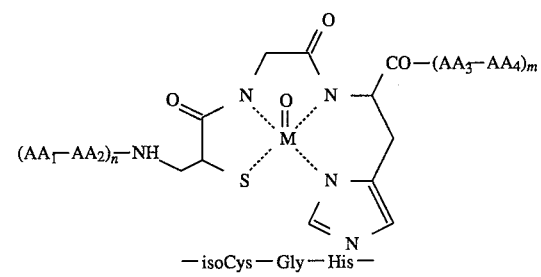

Wherein $(AA_1-AA_2)_n$ is a peptide chain of length n; $(AA_3-AA_4)_m$ is a peptide chain of length m; n and m may range from 0 to 20; and the sum n+m is greater than about 5 and less than about 20.

An important advantage of the peptide sequences used as ligand-forming spacer compounds according to the present invention is that the ligands may be incorporated into the peptides during peptide synthesis. Thus, the biologically active peptide and the ligand-forming spacer are synthesized together, in one step, using conventional peptide synthesis procedures and equipment, such as by solid phase synthesis. In this way, the separate step of incorporating the bifunctional chelate is avoided. Furthermore, a separate purification step of the peptide/bifunctional chelate conjugate is avoided according to the present invention.

From the foregoing, it will be appreciated that the present invention provides ligands capable of forming chelate complexes with diagnostic and therapeutic radioisotopes which can be incorporated directly into peptides at nonbiologically active locations and serve as bifunctional agents and as spacer molecules in the peptide.

The invention may be embodied in other specific forms without departing from its spirit or essential characteristics.

The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( D ) OTHER INFORMATION:
            Glu in location 4 is glutamic acid in which
            the gamma acid group is used to form the
            peptide bond ( x i ) SEQUENCE DESCRIPTION: SEQ ID NO:1:

Cys  Gly  Gly  Glu ( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( D ) OTHER INFORMATION:
            "Xaa" is lysine in which the epsilon amine is
            reacted with one acid group of succinic
            acid, leaving the other succinic acid group
            available to form the peptide bond ( x i ) SEQUENCE DESCRIPTION: SEQ ID NO:2:

Cys  Gly  Gly  Xaa

What is claimed is:

1. A peptide having the following general formula:

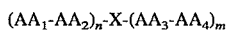

wherein X is a ligand selected from -Cys-Gly-Glu($\gamma$-)CO- (SEQ ID NO:1) and -Cys-Gly-Gly-Gly-Lys($\epsilon$-)NH-CO(CH$_2$)$_3$-CO- (SEQ ID NO:2), wherein $(AA_1-AA_2)_n$ is a peptide chain of length n; $(AA_3-AA_4)_m$ is a peptide chain of length m; n and m range from 0 to 20; the sum n+m is greater than 5 and less than or equal to 20; and wherein either $(AA_1-AA_2)_n$ or $(AA_3-AA_4)_m$ has biological binding activity.

2. A peptide having the following general formula:

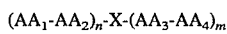

wherein X is a ligand selected from -Cys-Gly-(imidazolyl glycyl)-, isoCys-Gly-(imidazolyl glycyl)-, and -isoCys-Gly-His-, wherein $(AA_1-AA_2)_n$ is a peptide chain of length n; $(AA_3-AA_4)_m$ is a peptide chain of length m; n and m range from 0 to 20; the sum n+m is greater than 5 and less than or equal to 20; and wherein either $(AA_1-AA_2)_n$ or $(AA_3-AA_4)_m$ has biological binding activity.

3. A peptide having the following general formula:

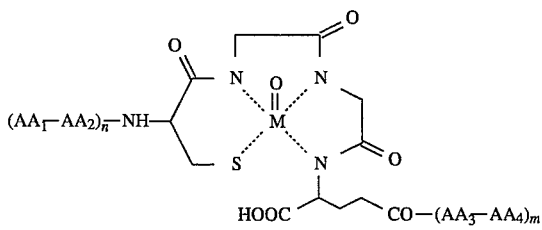

Wherein $(AA_1-AA_2)_n$ is a peptide chain of length n; $(AA_3-AA_4)_m$ is a peptide chain of length m; n and m range from 0 to 20 and the sum n+m is greater than 5 and less than or equal to 20; M is a radionuclide; and wherein either $(AA_1-AA_2)_n$ or $(AA_3-AA_4)_m$ has biological binding activity.

4. A peptide having the following general formula:

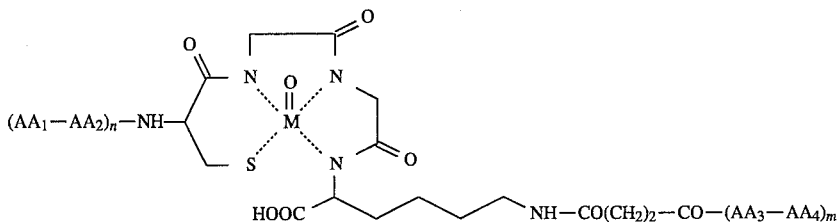

wherein $(AA_1\text{-}AA_2)_n$ is a peptide chain of length n; $(AA_3\text{-}AA_4)_m$ is a peptide chain of length m; n and m range from 0 to 20 and the sum n+m is greater than 5 and less than or equal to 20; M is a radionuclide; and wherein either $(AA_1\text{-}AA_2)_n$ or $(AA_3\text{-}AA_4)_m$ has biological binding activity.

5. A peptide having the following general formula:

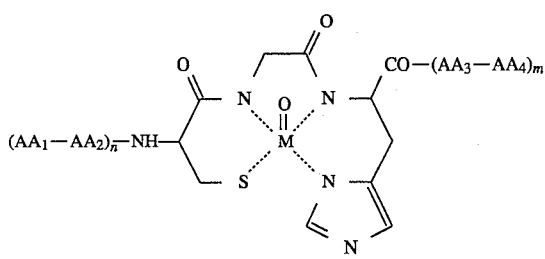

wherein $(AA_1\text{-}AA_2)_n$ is a peptide chain of length n; $(AA_3\text{-}AA_4)_m$ is a peptide chain of length m; n and m range from 0 to 20 and the sum n+m is greater than 5 and less than or equal to 20; M is a radionuclide; and wherein either $(AA_1\text{-}AA_2)_n$ or $(AA_3\text{-}AA_4)_m$ has biological binding activity.

6. A peptide having the following general formula:

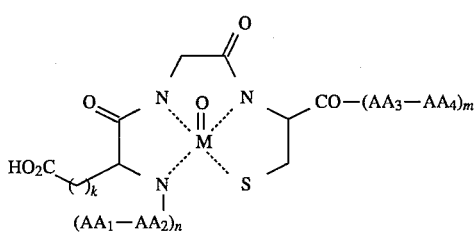

wherein $(AA_1\text{-}AA_2)_n$ is a peptide chain of length n; $(AA_3\text{-}AA_4)_m$ is a peptide chain of length m; n and m range from 0 to 20 and the sum n+m is greater than 5 and less than or equal to 20; M is a radionuclide; and wherein either $(AA_1\text{-}AA_2)_n$ or $(AA_3\text{-}AA_4)_m$ has biological binding activity.

7. A peptide having the following general formula:

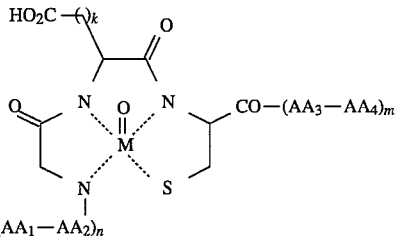

wherein $(AA_1\text{-}AA_2)_n$ is a peptide chain of length n; $(AA_3\text{-}AA_4)_m$ is a peptide chain of length m; n and m range from 0 to 20 and the sum n+m is greater than 5 and less than or equal to 20; M is a radionuclide; and wherein either $(AA_1\text{-}AA_2)_n$ or $(AA_3\text{-}AA_4)_m$ has biological binding activity.

8. A peptide having the following general formula:

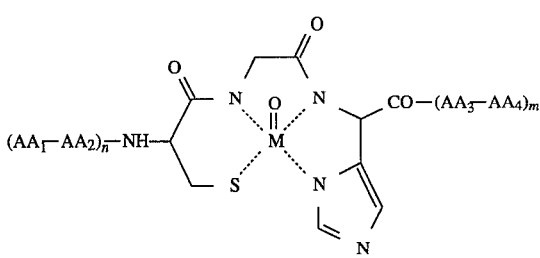

wherein $(AA_1\text{-}AA_2)_n$ is a peptide chain of length n; $(AA_3\text{-}AA_4)_m$ is a peptide chain of length m; n and m range from 0 to 20 and the sum n+m is greater than 5 and less than equal to 20; M is a radionuclide; and wherein either $(AA_1\text{-}AA_2)_n$ or $(AA_3\text{-}AA_4)_m$ has biological binding activity.

9. A peptide having the following general formula:

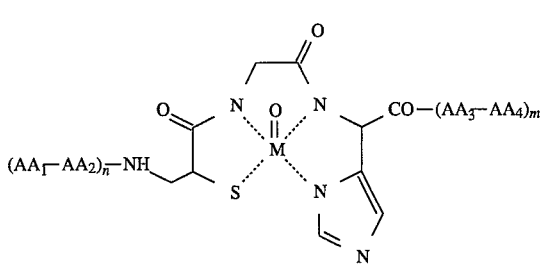

wherein $(AA_1\text{-}AA_2)_n$ is a peptide chain of length n; $(AA_3\text{-}AA_4)_m$ is a peptide chain of length m; n and m range from 0 to 20 and the sum n+m is greater than 5 and less than or equal to 20; M is a radionuclide; and wherein either $(AA_1\text{-}AA_2)_n$ or $(AA_3\text{-}AA_4)_m$ has biological binding activity.

10. A peptide having the following general formula:
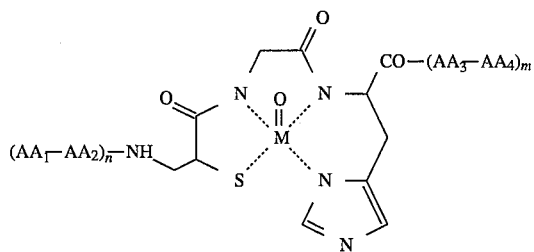
wherein $(AA_1-AA_2)_n$ is a peptide chain of length n; $(AA_3-AA_4)_m$ is a peptide chain of length m; n and m range from 0 to 20 and the sum n+m is greater than 5 and less than or equal to 20; M is a radionuclide; and wherein either $(AA_1-AA_2)_n$ or $(AA_3-AA_4)_m$ has biological binding activity.
* * * * *